US011857263B2

(12) United States Patent
Belson

(10) Patent No.: US 11,857,263 B2
(45) Date of Patent: Jan. 2, 2024

(54) PERSONALIZED ATRIAL FIBRILLATION ABLATION

(71) Applicant: Amir Belson, Los Altos, CA (US)

(72) Inventor: Amir Belson, Los Altos, CA (US)

( * ) Notice: Subject to any disclaimer, the term of this patent is extended or adjusted under 35 U.S.C. 154(b) by 385 days.

(21) Appl. No.: 16/077,381

(22) PCT Filed: Feb. 10, 2017

(86) PCT No.: PCT/US2017/017548
§ 371 (c)(1),
(2) Date: Aug. 10, 2018

(87) PCT Pub. No.: WO2017/139693
PCT Pub. Date: Aug. 17, 2017

(65) Prior Publication Data
US 2019/0046270 A1 Feb. 14, 2019

Related U.S. Application Data

(60) Provisional application No. 62/293,339, filed on Feb. 10, 2016.

(51) Int. Cl.
*A61B 18/14* (2006.01)
*A61B 34/10* (2016.01)
(Continued)

(52) U.S. Cl.
CPC .......... *A61B 34/10* (2016.02); *A61B 18/1492* (2013.01); *A61B 2017/00526* (2013.01);
(Continued)

(58) Field of Classification Search
CPC ...... A62B 19/1492; A61B 2018/00577; A61B 18/12; A61B 18/14; A61B 2018/00369; A61B 2018/00351
See application file for complete search history.

(56) References Cited

U.S. PATENT DOCUMENTS 6,120,496 A * 9/2000 Whayne ............. A61B 18/1492
128/DIG. 26
8,016,882 B2 * 9/2011 Macoviak ............. A61F 2/2445
623/2.36
(Continued)

FOREIGN PATENT DOCUMENTS

WO WO-2016060983 A1 * 4/2016 ......... A61B 18/1206

*Primary Examiner* — Joseph A Stoklosa
*Assistant Examiner* — Annie L Shoulders
(74) *Attorney, Agent, or Firm* — GSS Law Group

(57) ABSTRACT

Devices and methods are described for treatment of cardiac arrhythmias, particularly atrial fibrillation. A three-dimensional computer model of the patient's heart produced from imaging data is used to fabricate a personalized or patient-specific customized ablation catheter. The personalized ablation catheter is shaped to fit the unique anatomy of the patient's left atrium and has ablation elements that correspond with each of the patient's pulmonary vein ostia. Ostial fitment elements engage the ostia to align the ablation elements and a base ring attached by spring members urges the ablation elements into apposition with the inner wall of the left atrium. A neuroprotective mesh is attached across the ring to capture and remove potential emboli. Ablation energy, such as radiofrequency energy, is applied through the ablation elements. Electrodes located on the personalized ablation catheter are used to verify electrical isolation of the pulmonary veins at the completion of the procedure.

13 Claims, 13 Drawing Sheets

(51) Int. Cl.
  *A61B 90/00* (2016.01)
  *A61B 17/00* (2006.01)
  *A61B 18/00* (2006.01)
  *A61M 25/00* (2006.01)

(52) U.S. Cl.
  CPC .............. *A61B 2018/00375* (2013.01); *A61B 2018/00577* (2013.01); *A61B 2034/104* (2016.02); *A61B 2034/105* (2016.02); *A61B 2090/374* (2016.02); *A61B 2090/378* (2016.02); *A61B 2090/3762* (2016.02); *A61M 25/0009* (2013.01)

(56) References Cited

U.S. PATENT DOCUMENTS

| | | | | |
|---|---|---|---|---|
| 2003/0060821 A1* | 3/2003 | Hall | .................. | A61B 18/1492 606/41 |
| 2005/0228468 A1* | 10/2005 | Macoviak | .......... | A61B 18/1492 607/119 |
| 2007/0265610 A1* | 11/2007 | Thapliyal | ........... | A61B 18/1492 606/27 |
| 2010/0030204 A1* | 2/2010 | Stein | .................. | A61M 25/1002 604/8 |
| 2011/0276047 A1* | 11/2011 | Sklar | ..................... | A61F 5/0127 606/41 |
| 2014/0114304 A1* | 4/2014 | Wang | ................. | A61B 18/1492 606/41 |
| 2015/0066010 A1* | 3/2015 | McLawhorn | ...... | A61B 18/1492 606/34 |
| 2015/0150643 A1* | 6/2015 | Trayanova | ............. | A61B 34/10 606/34 |
| 2015/0182740 A1* | 7/2015 | Mickelsen | ........ | A61M 25/0606 604/506 |
| 2015/0190616 A1* | 7/2015 | Salvestro | ........... | A61B 18/1492 604/175 |
| 2017/0265938 A1* | 9/2017 | Spence | ............. | A61B 18/1492 |

* cited by examiner

Image A          Image B

PERSONALIZED ATRIAL FIBRILLATION ABLATION

FIELD OF THE INVENTION

The present invention relates to methods and devices for treatment of cardiac arrhythmias, particularly atrial fibrillation. More specifically, it relates to an ablation treatment for atrial fibrillation that utilizes a three-dimensional model of the patient's heart to produce a personalized or patient-specific customized ablation catheter.

BACKGROUND OF THE INVENTION

At least 5 million people in the US alone suffer from atrial fibrillation. It represents by far the most relevant heart rhythm related clinical issue due to its complications including stroke, heart failure and increased risk of death. These complications are more frequent in less healthy individuals, such as patients over age 75, with diabetes, heart failure or heart valve malfunction. In many cases, the condition can be controlled with medications, either by reducing the heart rate ("rate control") or by maintaining a regular rhythm ("rhythm control"). In a significant proportion of patients, drugs are either ineffective or lead to unacceptable side effects. In those cases, electrophysiology-based treatment modalities such as ablation treatment may be employed.

Currently, many specialization centers throughout the world, and particularly in the US, Europe and South America, are dedicated to the safe and effective use of electrophysiology ablation procedures for treatment of arrhythmias. Ablation procedures are performed in an electrophysiology lab. It is currently recommended that ablation procedures be carried out with the help of a system for 3D electrical mapping of the heart to identify and locate the foci responsible for the arrhythmia. The most common form of ablation treatment for atrial fibrillation involves ablation of the pulmonary veins and surrounding tissue by means of radiofrequency energy.

Atrial fibrillation ablation can be performed from the inside of the heart via catheters that are introduced percutaneously from the veins in the groin or neck. Alternatively, it can be accomplished from the outside of the heart with either open heart surgery or via a thoracoscopic approach. A mixed or hybrid approach is also available. The most common approach is the catheter-based approach. This is considered a minimally-invasive procedure as no surgical incisions are required. The catheter that delivers the ablation energy can use radiofrequency or cryothermic energy. High intensity ultrasound and laser energy have also been used in the past. A standard ablation catheter is able to produce lesions only from its tip, which is from 4 to 8 mm long, shaped like a match head. The ablation points are centered in the left upper chamber of the heart, or left atrium. A series of ablation points is used to establish a line of lesions. These lines are supposed to block the trigger points of Atrial Fibrillation and create a barrier to the propagation of the arrhythmia. The lesions target the entrance of the pulmonary veins, of which usually two right and two left ones are found. The lesion points are applied inside the left atrium a few millimeters from the pulmonary vein insertion in the body of the left atrium. This region is known as the pulmonary vein antrum. The end point of the procedure is to electrically isolate the pulmonary veins—pulmonary vein isolation or PVI. A less common approach is to encircle both pulmonary vein orifices on one side with a single wider elliptical line, a technique called WACA or wide area circumferential ablation. Other lines of lesions and ablation points inside the left and right atrium are often made—mostly on the posterior wall and often also on other targets, such as the coronary sinus, the left atrial appendage base, the superior vena cava, the right atrial isthmus. The procedure takes between 2 and 4 hours and occasionally needs to be repeated. As a general rule, older patients with more heart disease and more frequent, longer episodes of atrial fibrillation require more extensive ablation procedures. The current recommendation for atrial fibrillation ablation requires documentation of successful isolation of the target areas with a circular mapping catheter and proof of block in cases where ablation lesions are delivered along a line (linear lesions). Radio frequency ablation of atrial fibrillation can also be performed with the help of stereotaxis navigation of the left atrium, which allows the ablation catheter to be moved within the atrial anatomy and controlled remotely from the patient operative bed, using a magnetic field to direct and gently steer the tip of the catheter into the appropriate sites of ablation.

The current approaches to ablation treatment of atrial fibrillation suffer from a number of drawbacks. First, the ablation procedure is very time-consuming as it requires electrophysical mapping of the patient's atrium, followed by point-by-point creation of circular and/or linear lesions using an electrode-tipped catheter. As noted above, the ablation procedure can require 2-4 hours for completion. Efforts have been made to develop a single-shot approach intended to shorten the procedure time. One approach is to use one or more multi-electrode catheters that are capable of creating longer ablation lesions. Thus far, this approach has achieved only modest reductions in procedure time.

In addition, the success rate for ablation treatment of atrial fibrillation is fairly low, typically around 60%. Repeat procedures are often necessary. Factors that have been identified as contributing to the low success rate include variations in the anatomy of the atrium and pulmonary veins and incomplete apposition of the ablation catheter to the target tissue. The present invention addresses these two shortcomings of existing approaches to ablation treatment of atrial fibrillation.

DESCRIPTION OF THE INVENTION

Figure 1:
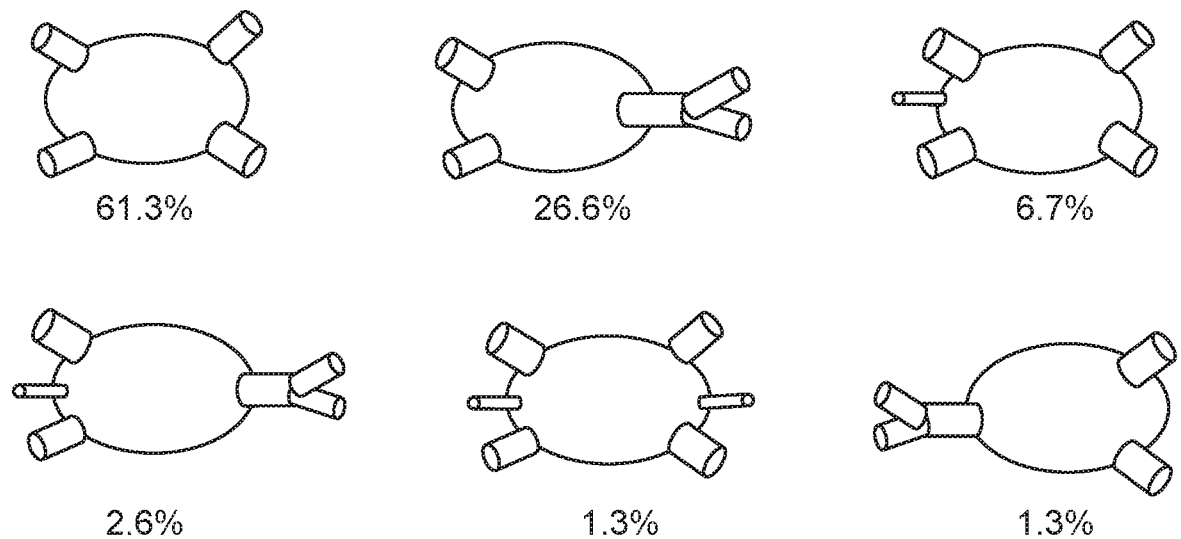
FIG. 1 is a graphic representation of variations in the left atrium and pulmonary vein anatomy.

Variations in the anatomy of the left atrium and pulmonary vein anatomy are much more common than was once believed. FIG. 1 is a graphic representation of the variations in the left atrium and pulmonary vein anatomy, as reported by Sohns et al in World Journal of Radiology (Sohns et al, World J Radiol 2011 Feb. 28; 3(2): 41-46). In this study, only about 61.3 percent of patients were found to have the classic textbook anatomy with four pulmonary veins connected to the left atrium. In the second most common variant, approximately 26.6 percent of patients had a left common trunk connecting the left pulmonary veins to the left atrium. Approximately 1.3 percent of patients had a right common trunk connecting the right pulmonary veins to the left atrium. As shown, other variations included one or more smaller, accessory pulmonary veins. Other studies have found similar percentages of atypical anatomy. Furthermore, even within these categories of anatomical variants, there can be considerable variation in terms of the size and location of the ostia of the pulmonary veins. Any of the pulmonary veins can be the location of arrythmogenic foci that give rise to anomalous electrical signals that are the cause of atrial fibrillation. Hunter et al reported that the single-procedure success rate for ablation treatment of atrial fibrillation was approximately 10 percent lower in patients with atypical anatomy of the pulmonary veins (Europace (2010) 12, 1691-1697). To be fully effective, ablation treatment must take these variations of anatomy into account. The one-size-fits-all approach of many existing devices may leave a significant number of patients inadequately treated.

Figure 2:
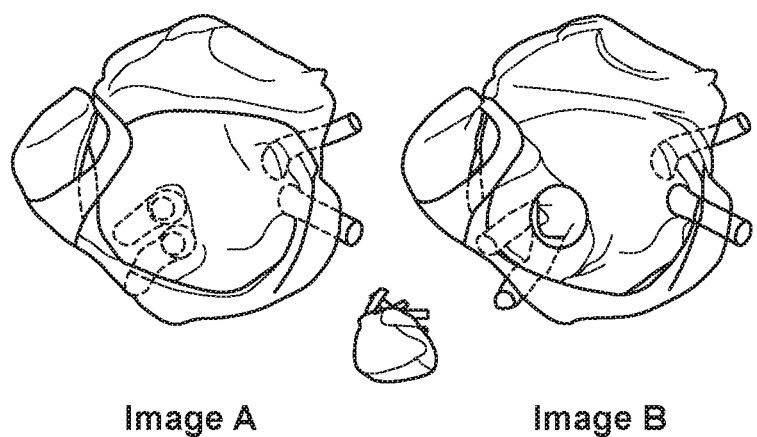
FIG. 2 shows images derived from three-dimensional imaging data illustrating two variants of pulmonary vein anatomy.

FIG. 2 shows images derived from three-dimensional imaging data, such as a CT scan or MRI, illustrating two variants of pulmonary vein anatomy. The reconstructed view is looking up at the roof of the atrium from inside the chamber of the atrium. Image A on the left illustrates the most common variant having four pulmonary veins connected to the left atrium. Dark circles are drawn around the ostia of the four pulmonary veins to show the desired areas for ablation. Image B on the right illustrates a less common variant having a shared ostium or common trunk connecting the two right pulmonary veins to the left atrium. Dark circles are drawn around the two ostia of the left pulmonary veins and the shared ostium of the right pulmonary veins to show the desired areas for ablation.

Figure 3:
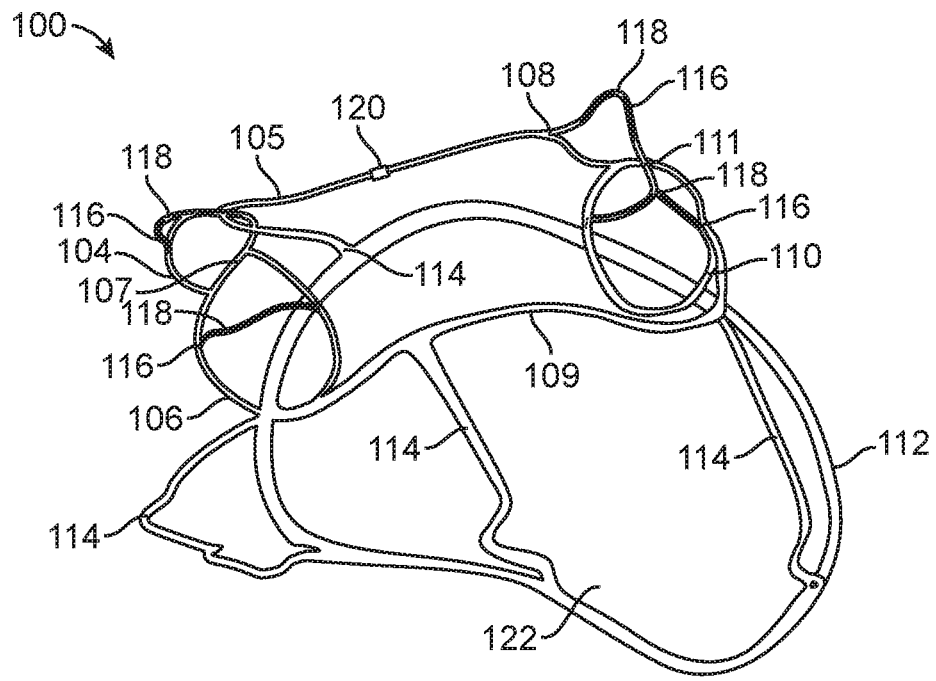
FIG. 3 shows an example of a personalized ablation catheter device for treatment of atrial fibrillation manufactured according to the present invention.
Figure 4:
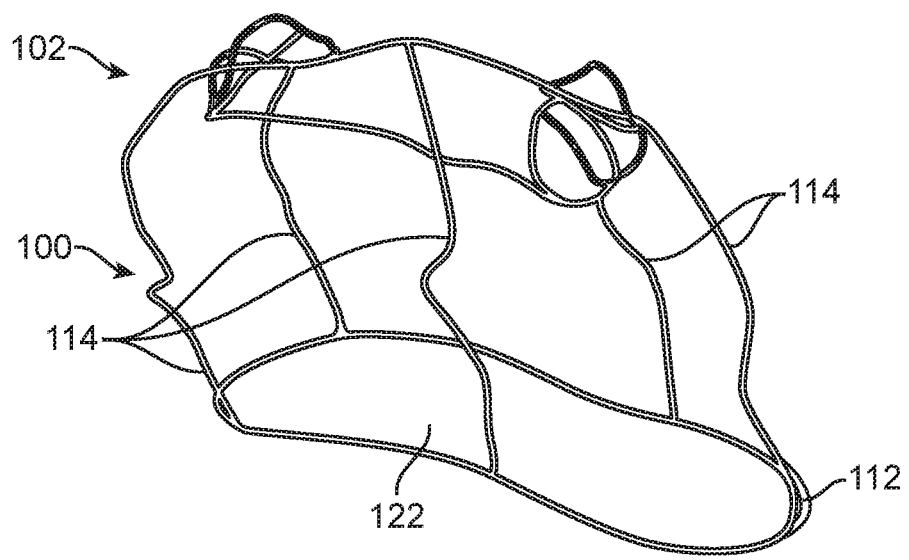
FIG. 4 is a side view of the personalized ablation catheter device of FIG. 5.

The present invention provides devices and methods for ablation treatment of atrial fibrillation that takes into account the variations of anatomy of the patient's left atrium and pulmonary veins for improved procedural efficacy. FIG. 3 shows an example of a personalized ablation catheter device 100 for treatment of atrial fibrillation manufactured according to the present invention. FIG. 4 is a side view of the personalized ablation catheter device 100 of FIG. 3. The personalized ablation catheter device 100 has an ablation panel 102 that is made up of multiple ablation elements. The number of ablation elements is determined by the number of pulmonary vein ostia connected to the atrium and any other desired areas for creating ablation lesions. In this illustrative example, a first ablation element 104 is configured to encircle the right superior pulmonary vein, a second ablation element 106 is configured to encircle the right inferior pulmonary vein, a third ablation element 108 is configured to encircle the left superior pulmonary vein, and a fourth ablation element 110 is configured to encircle the left inferior pulmonary vein. Naturally, if there are only three pulmonary vein ostia present because of a left or right common trunk, the ablation panel 102 would only have three of these ablation elements. More ablation elements can be added if there are other accessory pulmonary vein ostia present. Connecting members 105, 107, 109, 111 connect the ablation elements 104, 106, 108, 110 together to form the ablation panel 102. Because of anatomical variations, the size, shape and number of ablation elements 104, 106, 108, 110 and connecting members 105, 107, 109, 111 will vary. In some cases, the connecting members 105, 107, 109, 111 may be configured as linear ablation elements. These linear ablation elements can be used for example to create a box lesion to electrically isolate the entire area between the pulmonary veins when clinically indicated. These and other variations can be made to personalize the ablation catheter device 100 to the specific patient's anatomy.

The ablation elements are made of an electrically conductive material and are connected to a source of ablation energy by an electrical lead in the shaft of the ablation catheter device (not shown in this view). The ablation elements can be formed from one continuous loop of wire or each ablation element can be formed from a separate wire so that each ablation element can be energized selectively. In an alternative configuration, the ablation elements may have a multiplicity of ring-shaped electrodes spaced along a polymer catheter body. The ring-shaped electrodes may be separately connected to the ablation energy source so that they can be selectively energized to create a desired pattern of ablation lesions.

For effective ablation of the pulmonary veins, the ablation panel 102 must be well apposed to the wall of the atrium. For this purpose, the personalized ablation catheter device 100 includes a base ring 112 that is configured to seat around the periphery of the patient's mitral valve. The ablation panel 102 is connected to the ring 112 by spring members 114 that urge the ablation panel 102 into contact with the upper wall of the atrium. The base ring 112 and the spring members 114 can be constructed of a metal, such as stainless steel or a superelastic nickel-titanium alloy, a polymer, or a composite of different materials.

Additional features help to keep the ablation panel 102 aligned and apposed to the upper wall of the atrium. Ostial fitment elements 116 are connected to each of the ablation elements 104, 106, 108, 110 and are configured to engage each of the pulmonary veins to align the ablation elements with each of the ostia. The ostial fitment elements 116 protrude into the ostia of the pulmonary veins to help maintain this alignment. On each of the ostial fitment elements 116 is a trigger electrode 118 that contacts the tissue inside of the pulmonary veins. Additionally, there is at least one sensor electrode 120 on the device that contacts the wall of the atrium outside of the area to be electrically isolated by ablation. For example, a sensor electrode 120 may be located on one of the connecting members 105, 107, 109, 111.

Preferably, the personalized ablation catheter device 100 also provides a neuroprotective element, such as a neuroprotective mesh 122 that attaches across the base ring 112 to prevent potential emboli from entering the mitral valve. The mesh 122 will be made of a suitable woven, nonwoven or perforated material with pores sized to allow unimpeded blood flow while preventing passage of clots or other embolic particles above a certain size. For example, the mesh 122 may be a woven or nonwoven textile fabric made from natural, synthetic, polymeric or metallic fibers. This feature is especially advantageous because patients with atrial fibrillation are prone to forming clots within the atrium due to the inefficient pumping caused by the fibrillation. If these clots were to dislodge and flow to the brain, an embolic stroke could occur.

Preferably, the neuroprotective mesh 122 is also configured to capture and remove potential emboli. FIGS. 5A-5C and 6A-6B show two possible configurations for accomplishing this function.

Figure 5A:
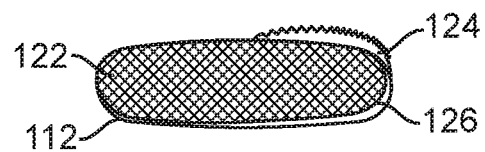
FIGS. 5A-5C illustrate a neuroprotective mesh which is a component of the personalized ablation catheter device.
Figure 5B:
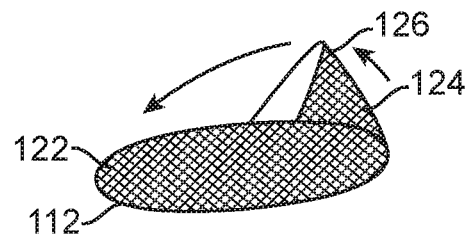
Figure 5C:
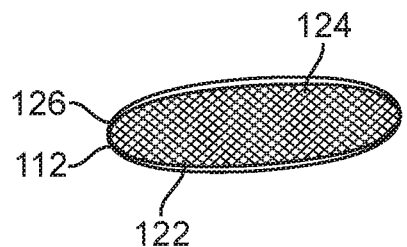

FIGS. 5A-5C show a neuroprotective element with a first layer of mesh 122 attached to the ring 112 of the ablation device as described above and a second layer of mesh 124 that is attached to a foldable wire rim 126. The foldable wire rim 126 is approximately semicircular with ends that are pivotally attached to the ring 112. When the device is first deployed, the second layer of mesh 124 is folded to the side, as shown in FIG. 5A, so that embolic particles can accumulate on the first layer of mesh 122. At the end of the procedure, prior to withdrawing the ablation device, the second layer of mesh 124 is closed over the first layer of mesh 122 by pivoting the foldable wire rim 126, as shown in FIG. 5B. A pull string or similar mechanism will be used to actuate the closing action. FIG. 5C shows the neuroprotective element in a closed position with any potential emboli trapped between the first layer of mesh 122 and the second layer of mesh 124.

Figure 6A:
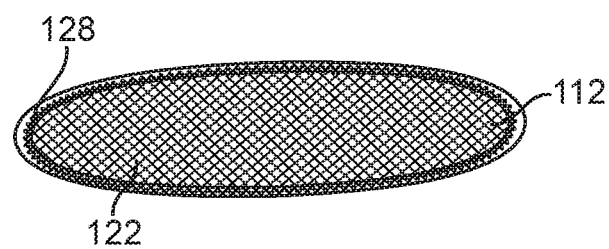
FIGS. 6A-6B shows how the neuroprotective mesh can be closed to capture emboli by pulling a purse string around the periphery of the mesh.
Figure 6B:
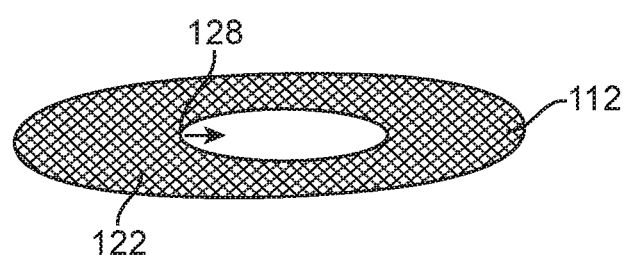

FIGS. 6A-6B show a neuroprotective element with a purse string 128 around the periphery of the neuroprotective mesh 122. The neuroprotective mesh 122 can be in a pouch-like configuration or it can be made in two layers as in the example described above. When the device is first deployed, the neuroprotective mesh 122 is gathered around the periphery of the ring 112 of the ablation device, as shown in FIG. 6A. At the end of the procedure, prior to withdrawing the ablation device, the neuroprotective mesh 122 is closed to trap any potential emboli by pulling the purse string 128, as shown in FIG. 6B.

Figure 7:
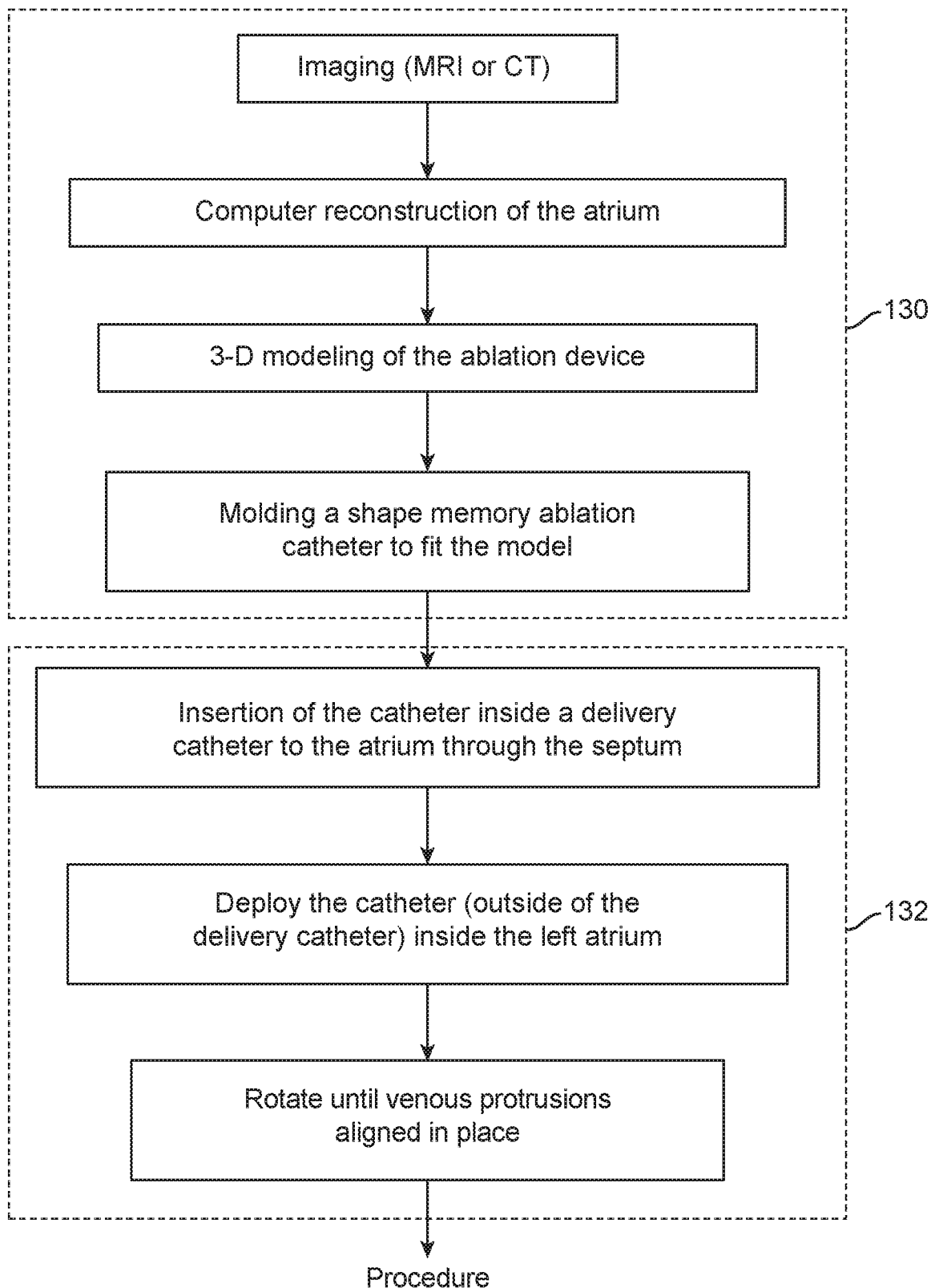
FIGS. 7 and 8 show a flowchart representing a method for manufacturing a personalized ablation catheter device according to the present invention and for ablation treatment of atrial fibrillation using the personalized ablation catheter device.
Figure 8:
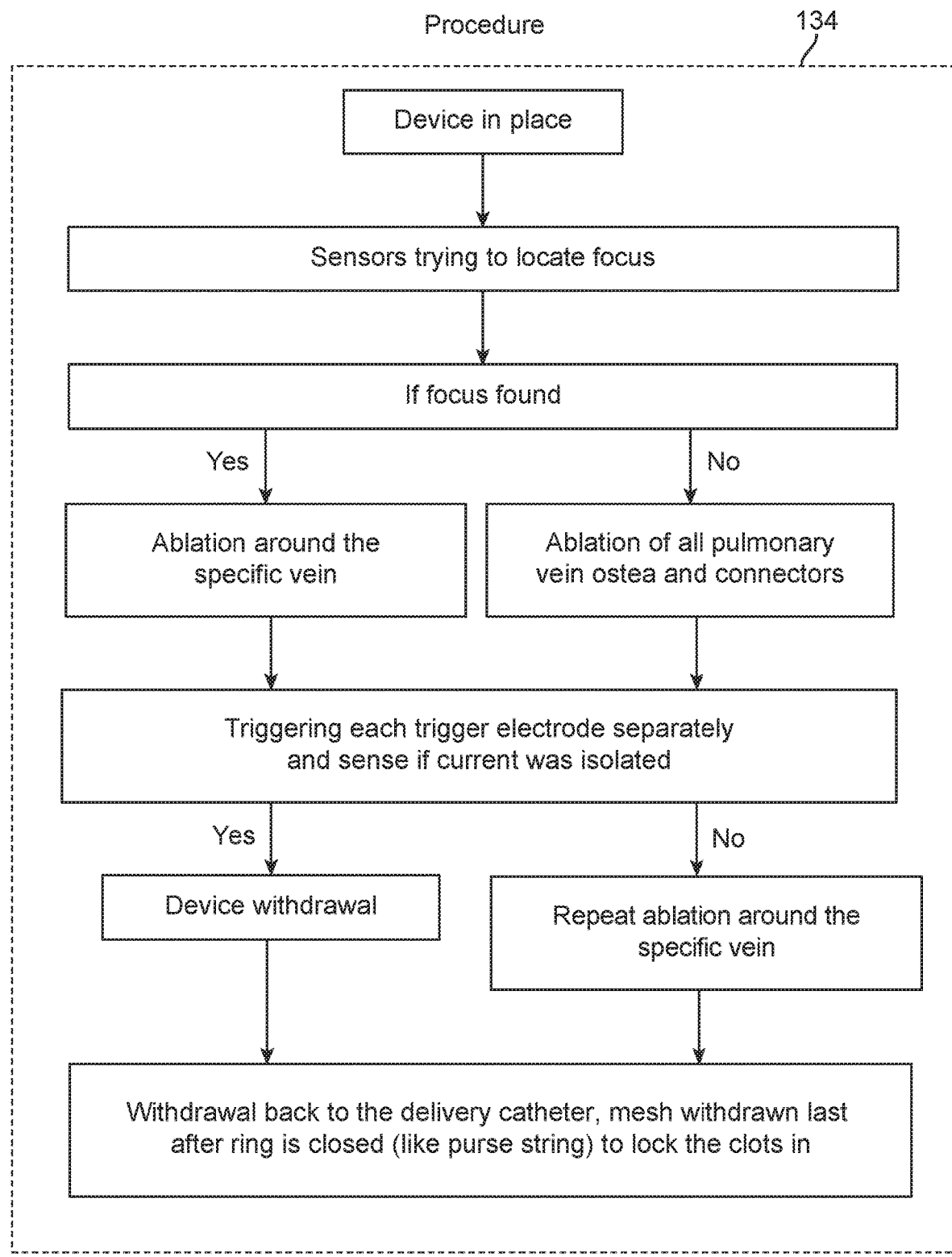

FIGS. 7 and 8 show a flowchart representing a method according to the present invention. The flowchart is divided into three portions, indicated by the large boxes drawn with dashed lines. The first portion 130 on the top of FIG. 7 shows the steps for manufacturing a personalized ablation catheter device. The second portion 132 on the bottom of FIG. 7 shows the steps for catheter placement. The third portion 134 in FIG. 8 shows the steps of a procedure or method for ablation treatment of atrial fibrillation using the personalized ablation catheter device. The steps of the method shown in the flowchart will be described in connection with FIGS. 9-24.

Figure 9:
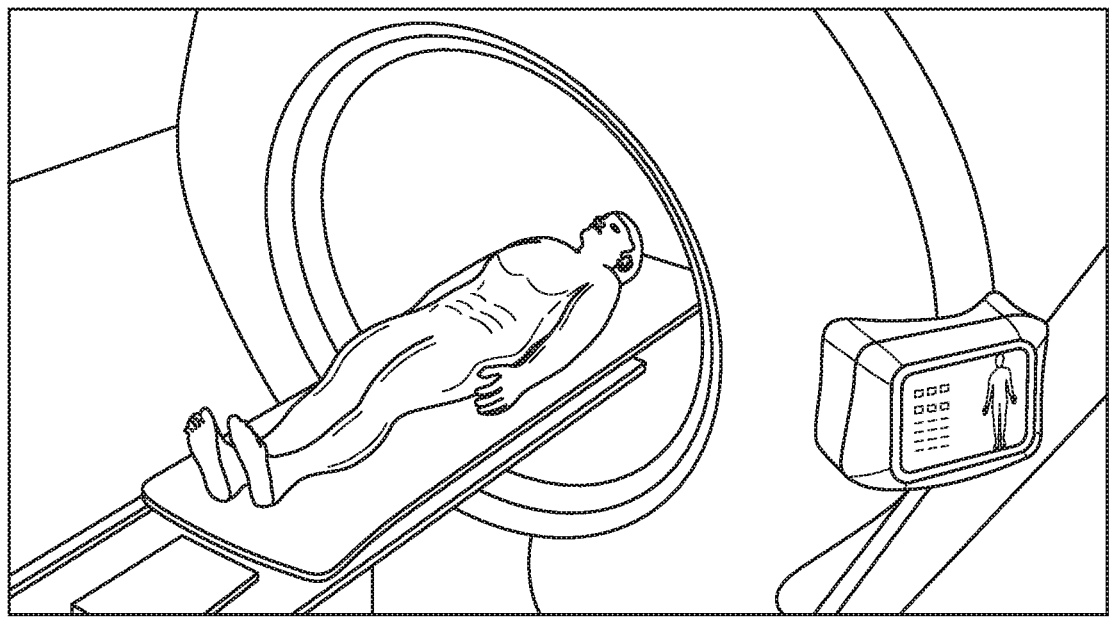
FIG. 9 represents the three-dimensional imaging step of the present invention.

A first step of the manufacturing method is depicted in FIG. 9 in which 3-D imaging is performed to determine the anatomy of the patient's heart, particularly the left atrium and pulmonary veins. The 3-D imaging may include computed axial tomography (CT) scanning, multidetector computed tomography (MDCT), magnetic resonance imaging (MRI), ultrasound cardiac imaging, transesophageal echocardiography (TEE) or other known imaging techniques.

Optionally, the anatomical imaging of the patient's left atrium and pulmonary veins can be combined with electrophysical mapping of the electrical activity of the patient's left atrium and pulmonary veins to locate suspected arrythmogenic foci. Electrophysical mapping can be performed with a multi-electrode sensing catheter.

Figure 10:
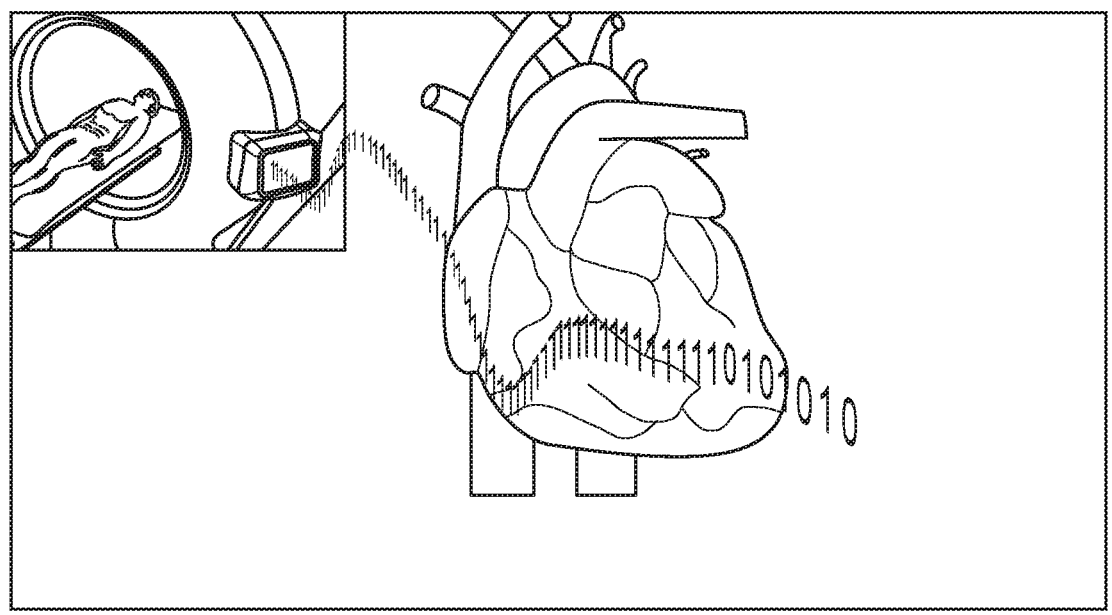
FIG. 10 represents a three-dimensional model of a patient's heart.

A 3-D computer model of the patient's left atrium and pulmonary veins is reconstructed Based on the 3-D imaging study, as represented in FIG. 10.

Figure 11:
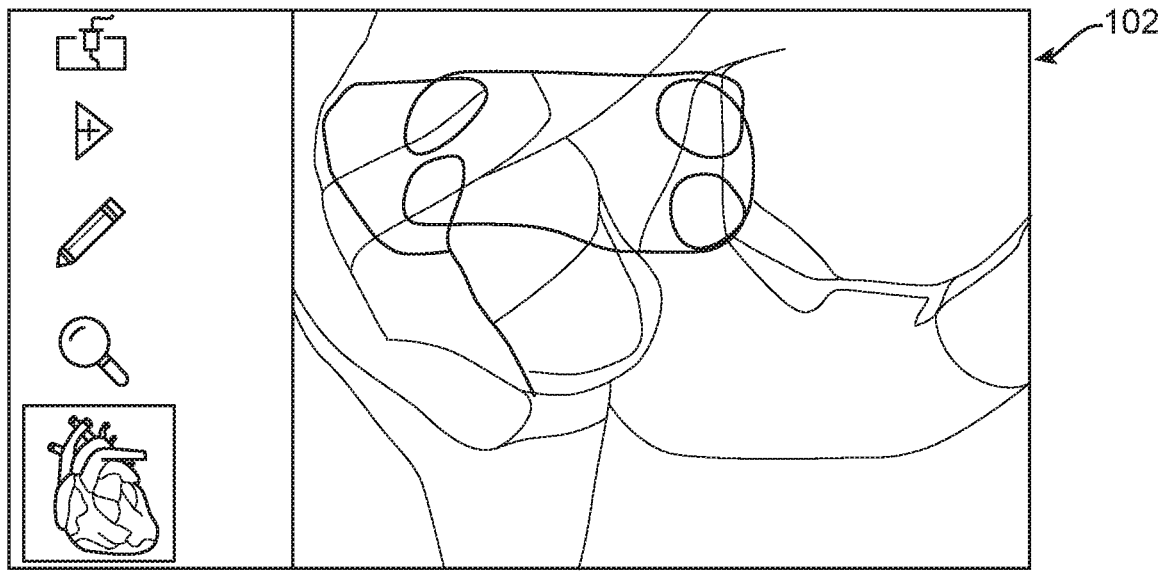
FIG. 11 shows an ablation panel of the personalized ablation catheter device being designed based on the three-dimensional model of a patient's heart.
Figure 12:
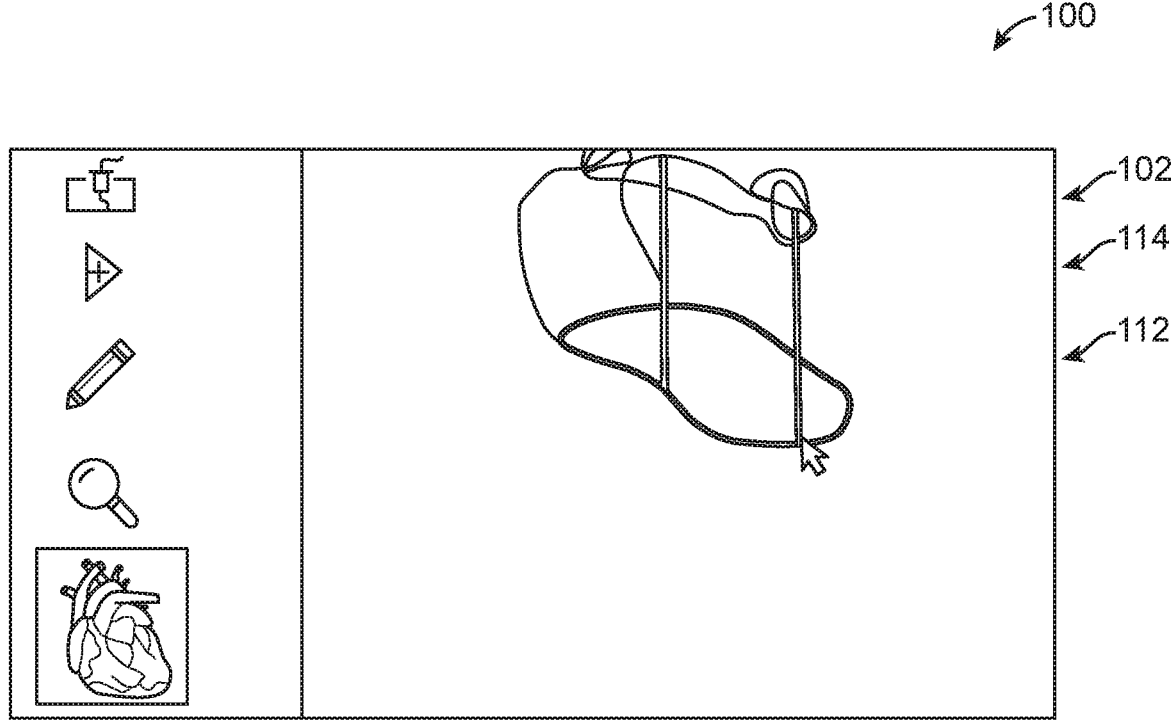
FIG. 12 shows the mesh ring and spring elements of the personalized ablation catheter device being designed based on the three-dimensional model of a patient's heart.

Then, 3-D modeling is used to design a personalized ablation catheter device that will create a desired pattern of ablation lesions based on the 3-D computer model of the patient's left atrium and pulmonary veins. The device design process can be done interactively on a computer. Alternatively, some or all of the device design process can be performed automatically by a computer. FIG. 11 shows a computer monitor where an ablation panel 102 of the personalized ablation catheter device is being designed based on the three-dimensional model of the patient's heart. The ablation elements in the ablation panel can be designed from scratch for each patient or the ablation elements and other components can be selected from a library of predesigned components. FIG. 12 shows the mesh ring 112 and spring elements 114 of the personalized ablation catheter device 100 being designed based on the three-dimensional model of the patient's heart. Similarly, the ring and the spring members can be designed from scratch or selected from a library of predesigned components.

Figure 13:
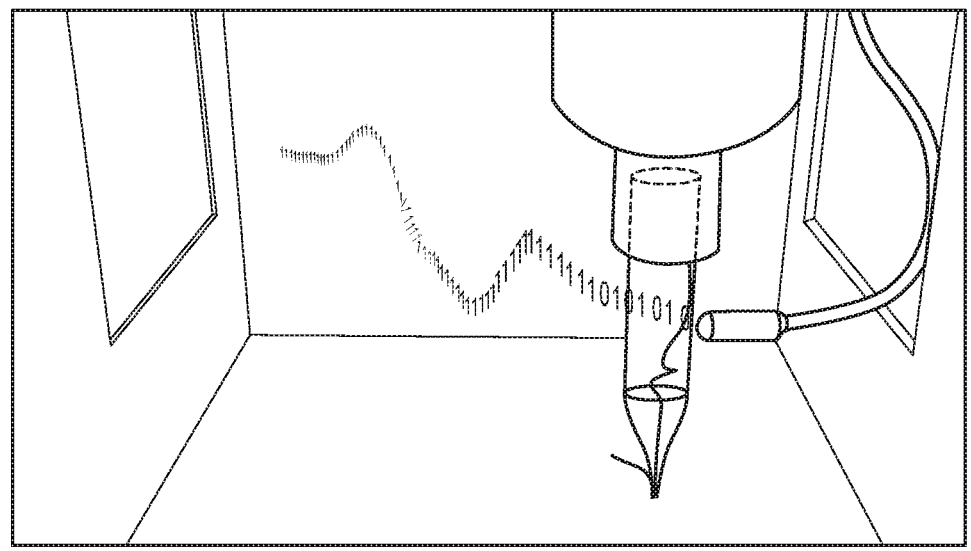
FIG. 13 represents the step of manufacturing the personalized ablation catheter device that has been designed based on the three-dimensional model of a patient's heart.

Next, a personalized patient-specific customized ablation catheter device 100 is fabricated that will create a desired pattern of ablation lesions according to the design that was based on the 3-D computer model of the patient's left atrium and pulmonary veins. FIG. 13 represents the step of manufacturing the personalized ablation catheter device that has been designed based on the three-dimensional model of a patient's heart. The personalized ablation catheter device can be manufactured using additive manufacturing, also known as 3-D printing, or using conventional fabrication techniques. Other fabrication techniques can be used such as wire bending and forming, polymer extrusion, heat forming, injection molding and CNC machining. Joining techniques such as welding, soldering, adhesive joining and fastener application can also be utilized.

Alternatively, 3-D printing or CNC machining can be used to create a physical model of the patient's atrium and pulmonary ostia as an aid to designing and fabricating a personalized ablation catheter device. As another alternative, 3-D printing or CNC machining can be used to create a mold for casting, molding or forming a personalized ablation catheter device or some of its components.

Figure 14:
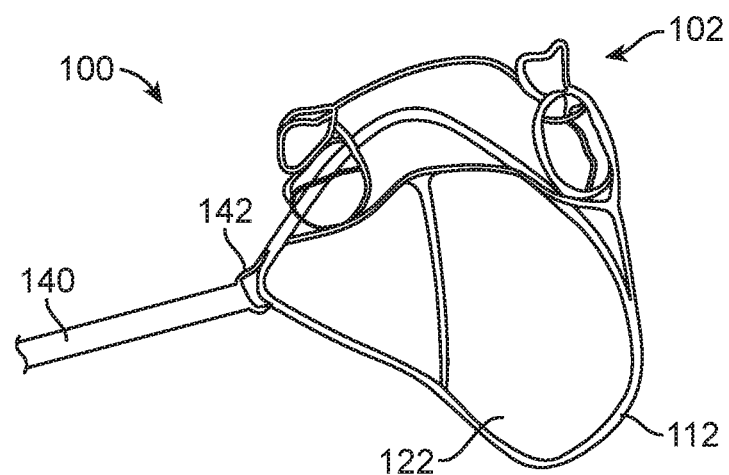
FIG. 14 shows the personalized ablation catheter device being loaded into a delivery catheter.

The neuroprotective mesh 122 is attached to the ring 112 and the ablation panel 102 is assembled to a catheter shaft 140 with electrical conductors 142 that are connected to the ablation elements, as shown in FIG. 14. The catheter shaft 140 will have suitable connectors on the proximal end for connecting to a source of ablation energy. After it is assembled, the personalized ablation catheter device 100 is compressed and loaded into a lumen of a delivery catheter 150 prior to use. The delivery catheter 150 can be seen in FIGS. 15-24.

In a variation of the manufacturing method, the personalized ablation catheter device can be fabricated from a catheter blank on which a desired curve is produced using mechanical and/or thermal shaping methods. The catheter blank is an electrode catheter that starts out straight or with no particular curve. Alternatively or in addition, the desired curve can be produced on a guidewire or stylet that is inserted into a flexible electrode catheter. 3-D printing can be used to add additional features, such as the base ring 112 and the spring members 114, to the catheter blank after it has been formed into a desired 3-D curve.

The method of catheter placement begins with the step of percutaneous delivery of the personalized ablation catheter device 100 into the patient's left atrium via a transeptal route. The delivery catheter 150 with the personalized ablation catheter device 100 compressed inside of the lumen is inserted percutaneously into a large vein such as the femoral vein or jugular vein and advanced to the patient's vena cava and into the right atrium under fluoroscopic guidance. The delivery catheter 150 is advanced across the atrial septum into the patient's left atrium.

Figure 15:
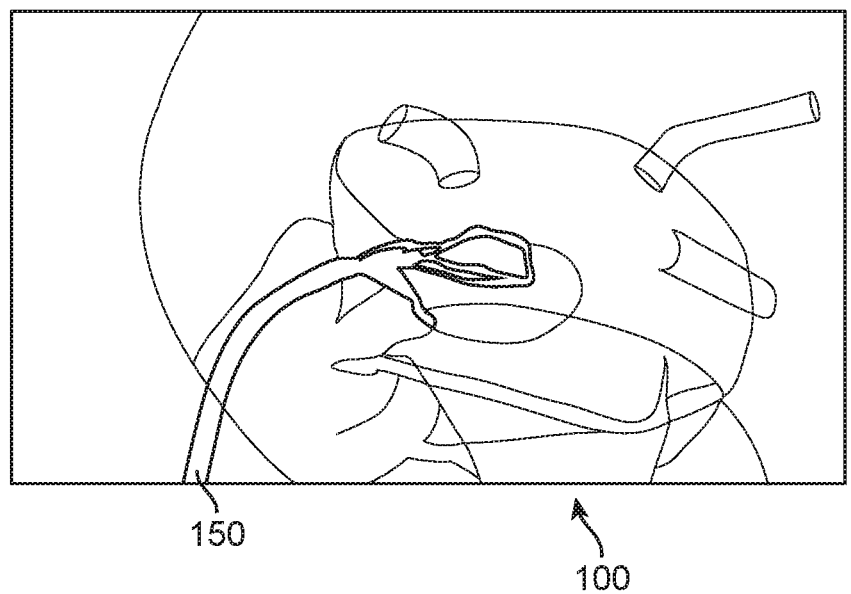
FIG. 15 shows the personalized ablation catheter device being delivered via a transeptal approach and deployed within the patient's left atrium.

Next, the personalized ablation catheter device 100 is deployed outside of the delivery catheter 150 inside the patient's left atrium. FIG. 15 shows the personalized ablation catheter device 100 being delivered via a transeptal approach and deployed within the patient's left atrium.

Figure 16:
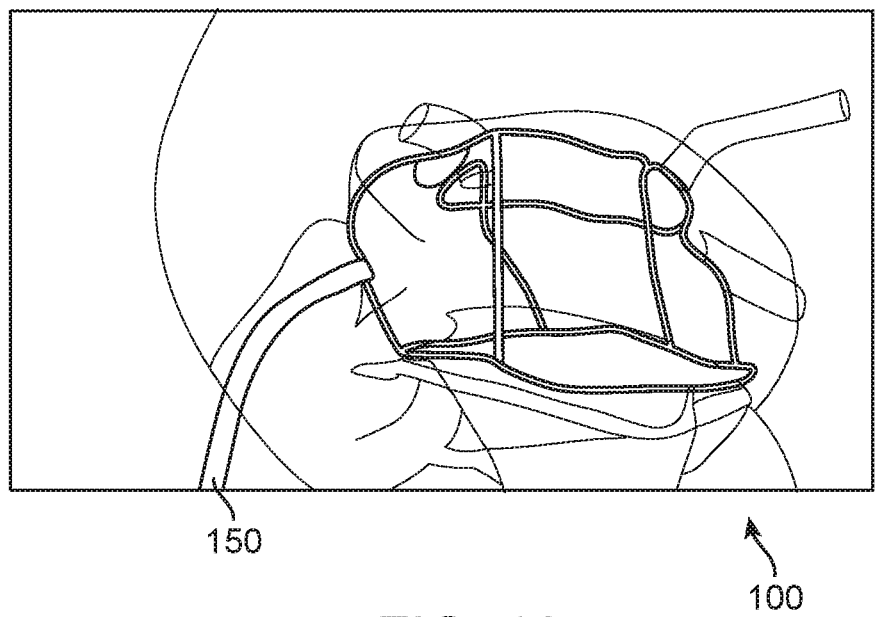
FIG. 16 shows the personalized ablation catheter device released within the patient's left atrium.

FIG. 16 shows the personalized ablation catheter device 100 released within the patient's left atrium. Once the personalized ablation catheter device 100 has expanded to its full size within the left atrium, the catheter device 100 is rotated until the protrusions of the ostial fitment members engage the ostia of the pulmonary veins and the ring 112 engages the periphery of the mitral valve for proper alignment and apposition of the ablation elements.

Figure 17:
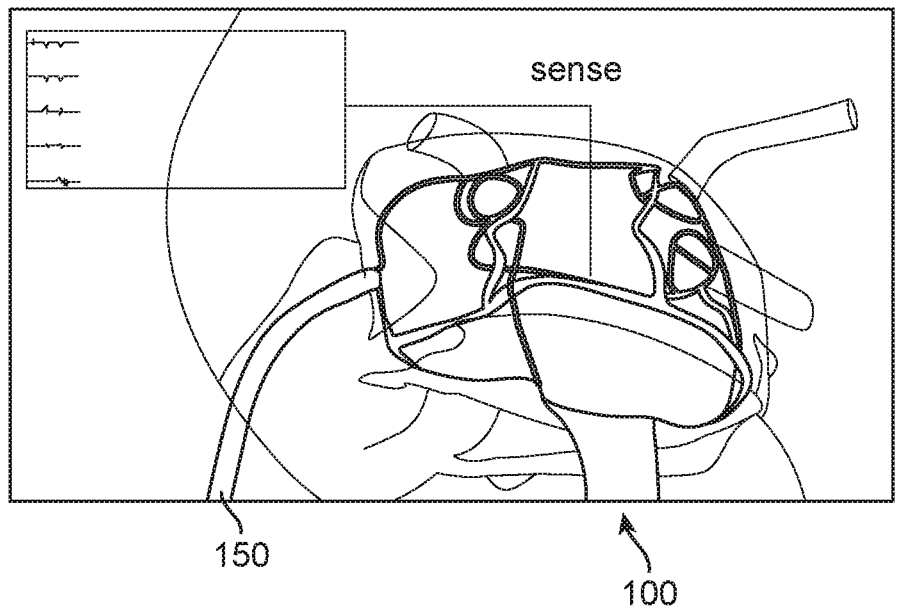
FIG. 17 shows the sensing electrode of the personalized ablation catheter device used to sense electrical signals indicative of the rhythm of the patient's heart beat.

The procedure or method for ablation treatment of atrial fibrillation described in the flowchart in FIG. 8 begins with the personalized ablation catheter device 100 in place within the patient's left atrium. As depicted in FIG. 17, the sensing electrode(s) of the personalized ablation catheter device 100 are used to sense electrical signals indicative of the rhythm of the patient's heart beat. If the patient is experiencing an arrhythmia, such as atrial fibrillation, this information will be used to help diagnose and locate any arrythmogenic foci.

Figure 18:
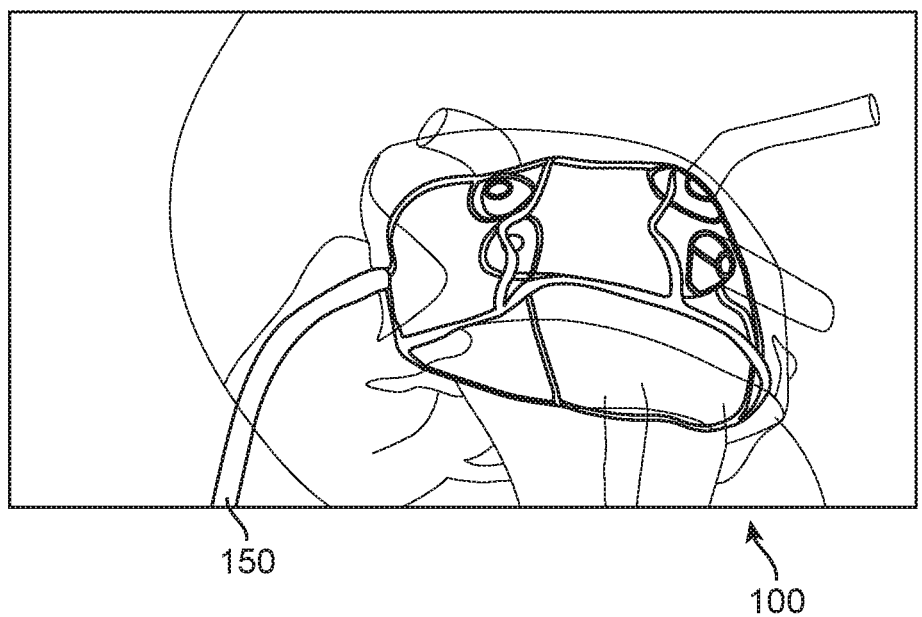
FIG. 18 shows the triggering electrode on the ostial fitment element applying triggering signals to see if it could trigger the arrhythmia so that the specific focus will be found and a target ablation around the specific ostium can be performed.

Next, a triggering signal is delivered through the triggering electrodes on each of the ostial fitment elements to see if it can trigger the arrhythmia so that the specific focus will be found and a target ablation around the specific ostium can be performed. FIG. 18 shows the triggering electrode on the ostial fitment elements applying the triggering signals.

Figure 19:
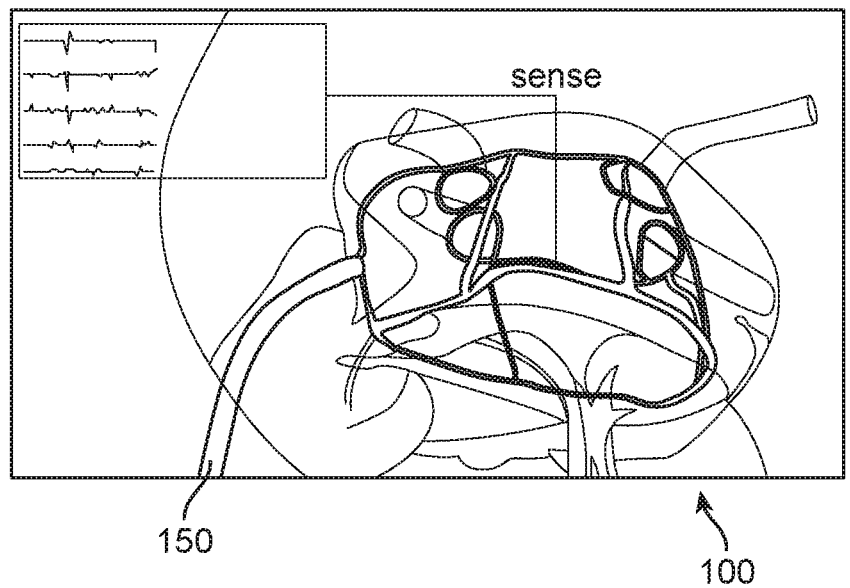
FIG. 19 shows the sensing electrode of the personalized ablation catheter device used to sense electrical signals that would indicate an arrhythmia had been triggered. If a specific focus is identified, the area around the corresponding pulmonary vein ostium will be ablated.
Figure 20:
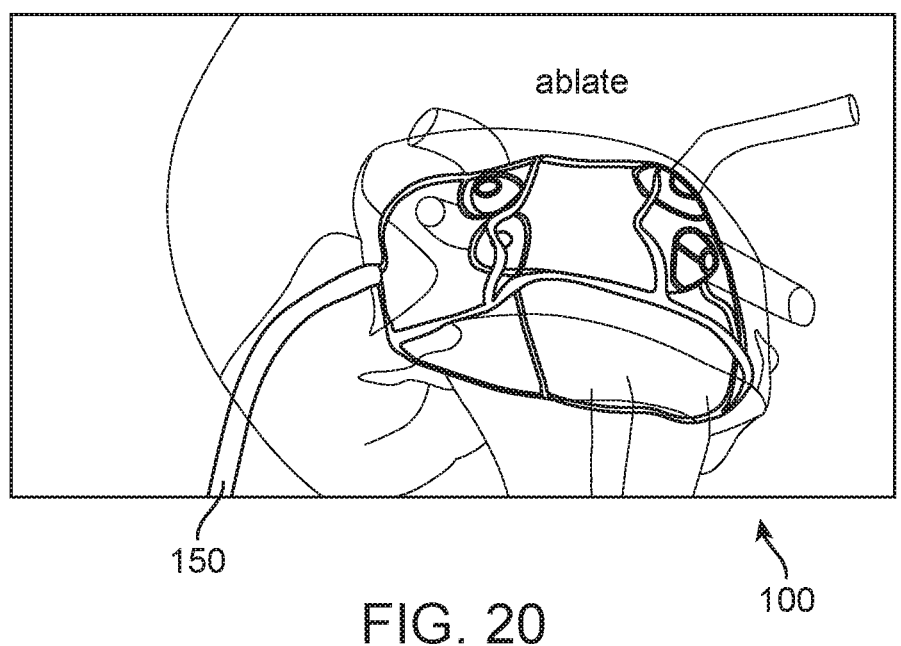
FIG. 20 shows that, if no specific focus is identified, an area around all of the pulmonary vein ostia will be ablated.

As depicted in FIG. 19, the sensing electrode(s) of the personalized ablation catheter device are used to sense electrical signals that would indicate an arrhythmia had been triggered. If a specific focus is identified, the area around the corresponding pulmonary vein ostium will be ablated, as shown in FIG. 20. If a specific focus is not identified, then the area around all of the pulmonary vein ostia will be ablated.

Ablation energy, for example radiofrequency energy, is applied through the ablation elements of the catheter to create a desired pattern of ablation lesions to block anomalous electrical signals that give rise to atrial fibrillation. Other modes of ablation energy can also be used, for example impulses of bipolar direct current can be applied through the ablation elements. Alternatively, cryogenic ablation energy can be used. In this case, the ablation catheter would be modified to allow a flow of cryogenic fluid through an internal lumen of the catheter for heat exchange with the wall of the atrium.

Figure 21:
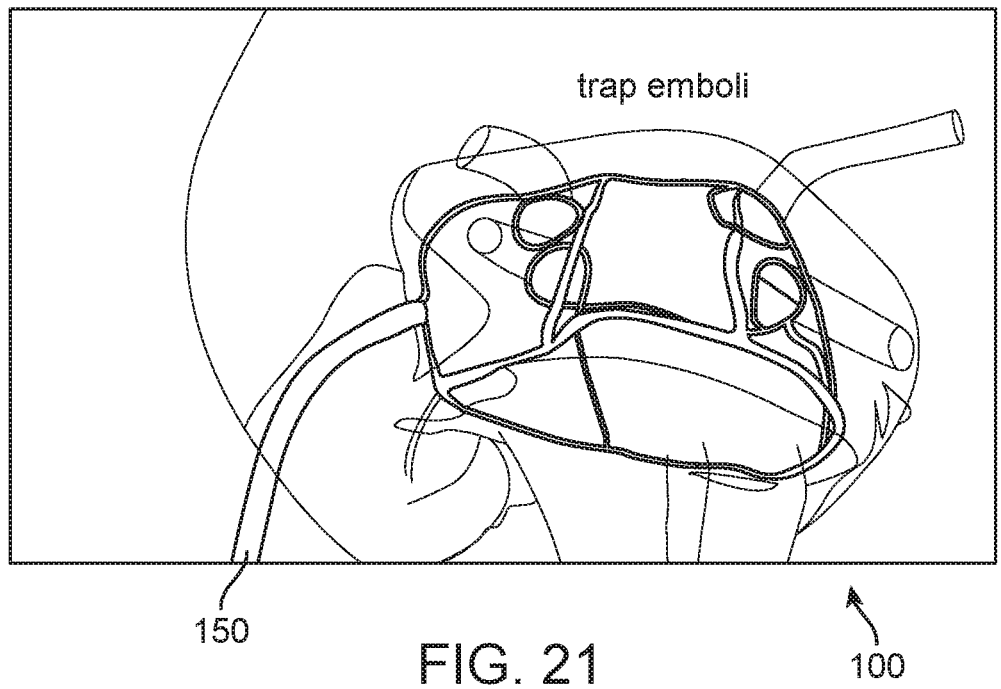
FIG. 21 shows how the neuroprotective mesh will capture potential emboli and other particles and debris.

During the procedure, any clots or other emboli that are created or dislodged within the atrium are caught by the neuroprotective mesh, as shown in FIG. 21.

Figure 22:
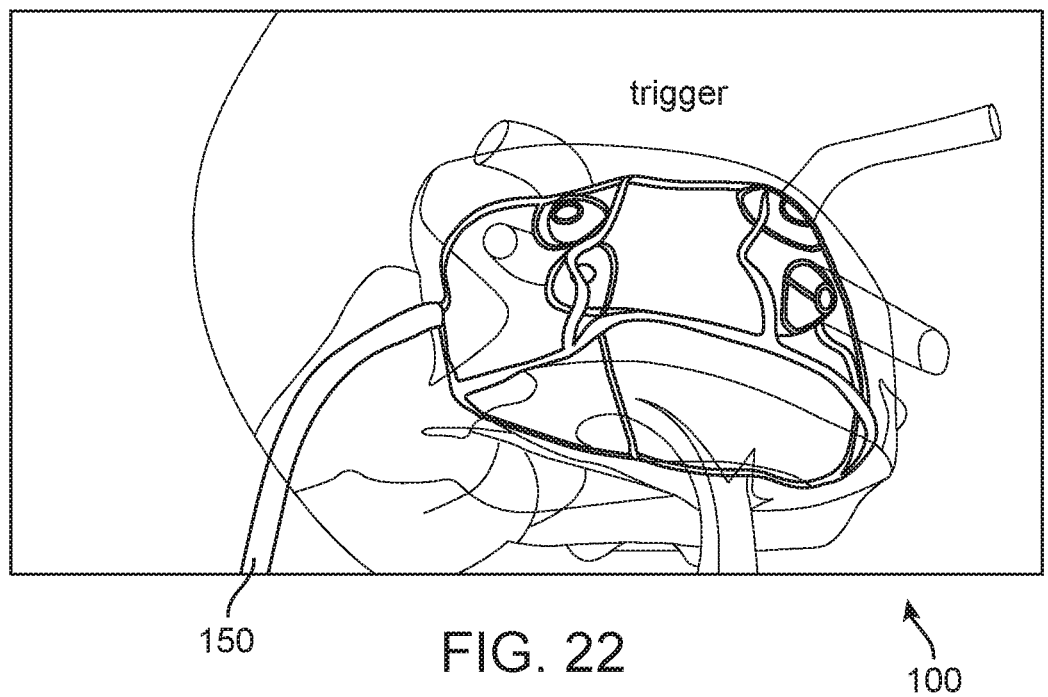
FIG. 22 shows that the triggering electrode in each of the pulmonary vein ostia will be triggered, either all together or separately.
Figure 23:
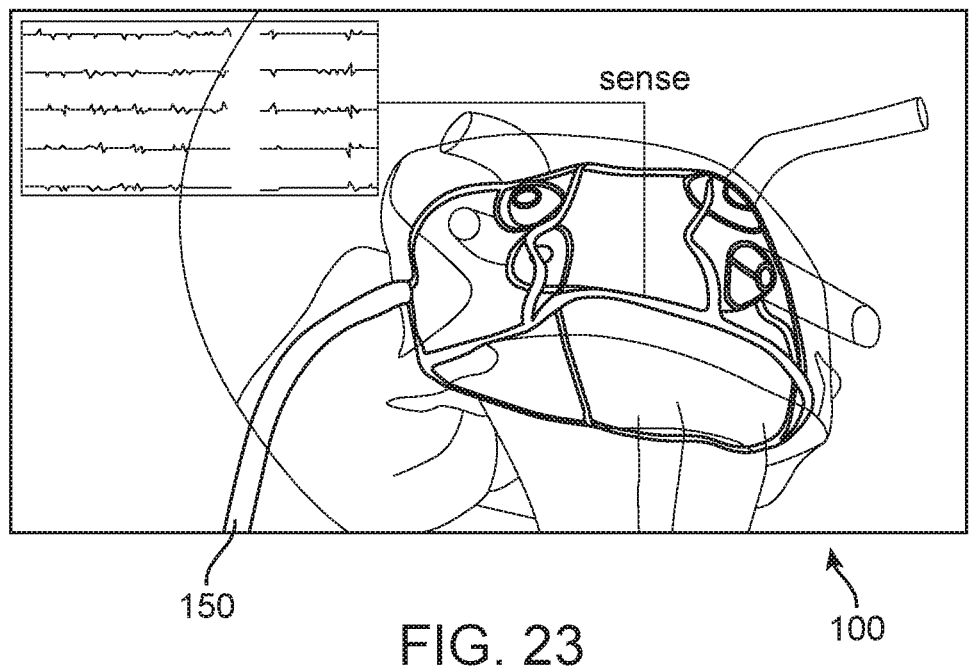
FIG. 23 shows that the sensing electrode of the personalized ablation catheter device is used to sense electrical signals to determine if the ablation procedure has been effective.
Figure 24:
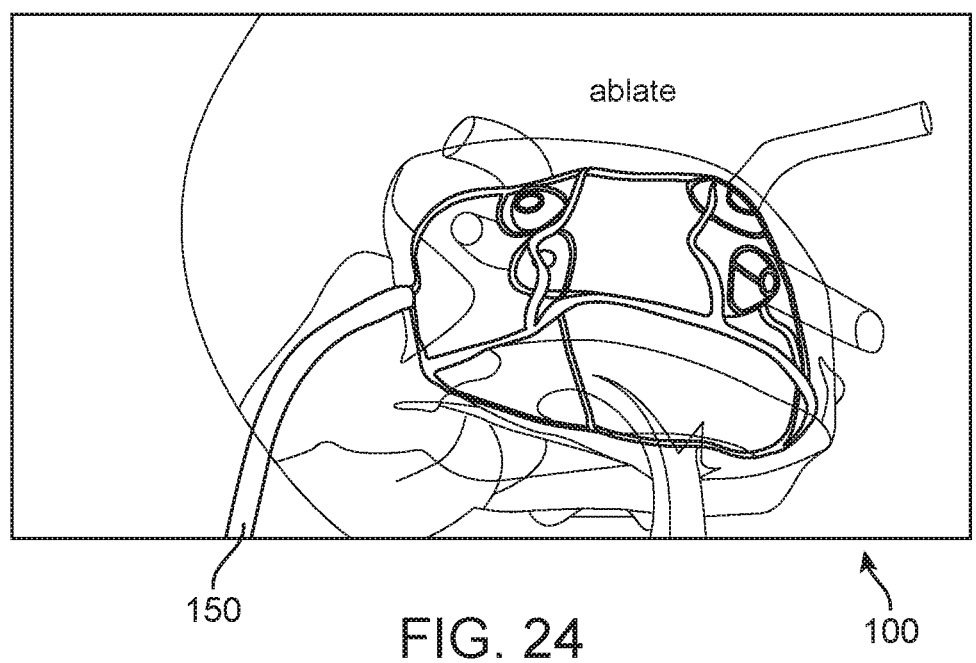
FIG. 24 shows that, if electrical signals are detected indicating that ablation is not complete, then repeat ablation will be applied.

After the ablation step, the trigger electrodes are used again to determine whether the pulmonary veins have been electrically isolated. As shown in FIG. 22, triggering signals are applied in each of the pulmonary veins, either all together or separately, while the sensing electrode(s) monitor the electrical signals, as shown in FIG. 23. If the sensing electrode(s) located outside of the ablation elements do not detect the triggering signal, it shows that the pulmonary veins have been electrically isolated and the procedure is completed. If, however, the triggering signal is detected by one or more of the sensing electrode(s), it shows that there is a current leak through or around one of the ablation lesions. In this case, the ablation is repeated in one or more of the pulmonary veins, as shown in FIG. 24, until electrical isolation is achieved.

Once electrical isolation of the pulmonary veins has been achieved, the personalized ablation catheter device is withdrawn into the delivery catheter. Prior to withdrawal, the neuroprotective mesh 112 is closed, as shown in FIG. 5C or 6B, to capture and remove any potential emboli.

The delivery catheter is then withdrawn and the venous puncture site is closed to achieve hemostasis.

It is expected that the devices and methods described herein will significantly reduce the procedure time required for atrial fibrillation ablation procedures while achieving greater procedural efficacy and reducing the need for repeat ablation procedures.

What is claimed is:

1. A personalized atrial fibrillation ablation device, comprising:
   an ablation panel configured to create a desired ablation pattern within a wall of a patient's left atrium to eliminate atrial fibrillation; wherein the ablation panel includes a first ablation element configured to encircle an ostium of a first pulmonary vein, a second ablation element configured to encircle an ostium of a second pulmonary vein, and a third ablation element configured to encircle an ostium of a third pulmonary vein, a first connecting member connecting the first ablation element to the second ablation element, and a second connecting member connecting the second ablation element to the third ablation element;

a base ring configured to seat around a periphery of the patient's mitral valve;

and at least one spring member connected between the ablation panel and the base ring and configured to urge the ablation elements of the ablation panel into contact with a portion of the wall of the patient's left atrium to be ablated.

2. The personalized atrial fibrillation ablation device of claim 1, wherein the ablation panel further comprises at least one ostial fitment element configured to engage at least one pulmonary vein to hold the ablation device in alignment with the patient's atrium.

3. The personalized atrial fibrillation ablation device of claim 1, wherein the ablation panel further comprises a multiplicity of ostial fitment elements configured to engage each of the pulmonary veins connected to the patient's left atrium.

4. The personalized atrial fibrillation ablation device of claim 1, further comprising:
a mesh material covering an opening within the base ring.

5. The personalized atrial fibrillation ablation device of claim 1, further comprising:
at least one trigger electrode configured to contact tissue on one side of an ablation pattern created by the ablation device and a sensing electrode configured to contact tissue on another side of the ablation pattern created by the ablation device.

6. The personalized atrial fibrillation ablation device of claim 1, wherein the ablation panel includes a fourth ablation element configured to encircle an ostium of a fourth pulmonary vein, and a third connecting member connecting the third ablation element to the fourth ablation element.

7. The personalized atrial fibrillation ablation device of claim 1, wherein the first ablation element, the second ablation element, and the third ablation element are constructed from a continuous wire of electrically conductive material.

8. The personalized atrial fibrillation ablation device of claim 7, wherein the first ablation element, the second ablation element, and the third ablation element are each configured to deliver radiofrequency ablation energy to create a desired ablation pattern within a wall of a patient's left atrium to eliminate atrial fibrillation;
and wherein the personalized atrial fibrillation ablation device includes a source of radiofrequency ablation energy electrically connected to the first ablation element, the second ablation element, and the third ablation element.

9. The personalized atrial fibrillation ablation device of claim 1, wherein the first ablation element, the second ablation element, and the third ablation element are each constructed from a separate wire of electrically conductive material such that each ablation element can be energized selectively.

10. The personalized atrial fibrillation ablation device of claim 9, wherein the first ablation element, the second ablation element, and the third ablation element are each configured to deliver radiofrequency ablation energy to create a desired ablation pattern within a wall of a patient's left atrium to eliminate atrial fibrillation;
and wherein the personalized atrial fibrillation ablation device includes a source of radiofrequency ablation energy electrically connected to the first ablation element, the second ablation element, and the third ablation element such that each ablation element can be energized selectively.

11. The personalized atrial fibrillation ablation device of claim 1, further comprising:
a delivery catheter, wherein the ablation panel is compressible to fit inside of a lumen within the delivery catheter.

12. A personalized atrial fibrillation ablation device, comprising:
an ablation panel configured to create a desired ablation pattern within a wall of a patient's left atrium to eliminate atrial fibrillation; wherein the ablation panel includes a first ablation element configured to encircle an ostium of a first pulmonary vein, a second ablation element configured to encircle an ostium of a second pulmonary vein, and a third ablation element configured to encircle an ostium of a third pulmonary vein, a first connecting member connecting the first ablation element to the second ablation element, and a second connecting member connecting the second ablation element to the third ablation element;

at least one ostial fitment element configured to engage at least one pulmonary vein to hold the ablation device in alignment with the patient's atrium;

a base ring configured to seat around a periphery of the patient's mitral valve and at least one spring element connected between the ablation panel and the base ring configured to hold the ablation elements of the ablation panel in contact with a portion of the atrial wall to be ablated;

a mesh material covering an opening within the base ring;

at least one trigger electrode configured to contact tissue on one side of an ablation pattern created by the ablation device and a sensing electrode configured to contact tissue on another side of the ablation pattern created by the ablation device;

and a delivery catheter, wherein the ablation element is compressible to fit inside of a lumen within the delivery catheter.

13. The personalized atrial fibrillation ablation device of claim 12, wherein the ablation panel includes a fourth ablation element configured to encircle an ostium of a fourth pulmonary vein, and a third connecting member connecting the third ablation element to the fourth ablation element.

* * * * *